United States Patent [19]

Rosenlicht

[11] Patent Number: 5,954,769
[45] Date of Patent: Sep. 21, 1999

[54] SURGICAL DRILL POSITIONING GUIDE

[76] Inventor: Joel L. Rosenlicht, 483 Middle Turnpike West, Manchester, Conn. 06040

[21] Appl. No.: 08/985,824

[22] Filed: Dec. 5, 1997

[51] Int. Cl.$^6$ .................. A61F 2/28; A61C 3/02
[52] U.S. Cl. .................. 623/16; 623/11; 433/76; 433/173; 433/180
[58] Field of Search .................. 623/11, 16, 17; 433/76, 180, 173

[56] References Cited

U.S. PATENT DOCUMENTS

| 0,655,933 | 8/1900 | Cron | 433/76 |
|---|---|---|---|
| 4,260,383 | 4/1981 | Weissman | 433/225 |
| 5,084,048 | 1/1992 | Jacob et al. | 606/61 |
| 5,215,460 | 6/1993 | Perry | 433/173 |
| 5,222,954 | 6/1993 | Baker et al. | 606/61 |
| 5,380,323 | 1/1995 | Howland | 606/61 |
| 5,427,906 | 6/1995 | Hansen | 433/173 |
| 5,460,526 | 10/1995 | Bosker | 433/173 |
| 5,564,928 | 10/1996 | Gittleman | 433/180 |
| 5,628,740 | 5/1997 | Mullane | 606/61 |
| 5,676,703 | 10/1997 | Gelbard | 623/17 |

FOREIGN PATENT DOCUMENTS

| 2671481 | 7/1992 | France | 433/180 |

*Primary Examiner*—Mickey Yu
*Assistant Examiner*—Dinh X. Nguyen

[57] ABSTRACT

Apparatus comprising drill guide bodies and a pair of positioning bars, each such drill guide body being a body so configured and constructed as to define an imaginary axis through the length thereof and forming a pilot guide bore for guiding a drill substantially along said axis and at least one lateral bore substantially perpendicular to said pilot guide bore substantially along chord of said drill guide body disposed on opposite sides of the pilot guide bore, and methods of forming stents and rigid guides for guiding the drilling of holes into a patient's boney structure are disclosed.

8 Claims, 3 Drawing Sheets

SURGICAL DRILL POSITIONING GUIDE

FIELD OF THE INVENTION

This invention relates to the installation of surgical appliances generally and specifically to surgical and dental prosthesis systems wherein bone screws, implants, magnets or other fasteners are used to affix the appliance permanently or temporarily to the bone of the patient.

BACKGROUND OF THE INVENTION

Many types of surgical and dental appliances are secured to the bone of the patient using bone screws, or other elongate fasteners. Bone nails or wires, usually supported by external or internal frames, e.g., the widely used Kirschner wire type devices are also commonly used.

One of the major problems the surgeon faces is the drilling of holes in the right location, properly spaced from each other and properly oriented relative to each other. Problems have been encountered in the past, for example, in drilling holes to receive bone fastening devices, i.e., devices to secure an appliance to the bone, such as bone screws, pins, wires and the like and in forming cavities for dental implants with a sufficient degree of precision, orientation and spacing.

Such holes, bores, recesses or passages are traditionally formed freehand. Of course, this can readily result in defective bores. There is a danger that the bore will be at such an inclination or position that the spongiosa or cortical bone or associated vascular or nerve tissue will be excessively damaged. Failure to maintain precision and spacing with respect to this dimension may be the cause of a variety of problems. Bone grafting or other procedures may be required to compensate for improper orientation or positioning of the implant cavity in the bone. Sometimes, once the damage has been caused, complete repair is not possible.

When the appliance is subjected to loading and when the screws or implants, for example, are not properly oriented there may be an element of transverse pressure transmission to the implant or fastener which can produce secondary infections and may lead to failure of the implant or fastener.

A feature of this invention is the provision of a quick, highly accurate, and inexpensive method and means for assuring proper spacing and orientation of holes to be drilled in a patient's bone to receive implants, screws, or other bone fasteners.

SUMMARY OF THE INVENTION

The invention is embodied in a stent for forming a rigid guide or a prosthesis that has a surface that is a reciprocal replication of the surface of a portion of a patient's boney structure into which holes are to be drilled at predetermined locations. The term reciprocal replication is used to mean a surface which will fit snugly against the surface of the patient's body into which holes are to be drilled. Thus, an impression mold taken of the surface of interest would reciprocally replicate the surface. In surgical procedures, it is frequently necessary that holes be drilled in a precise, predetermined position, spacing and orientation to match screw holes or wire holes or to permit the placement of screws, or other fasteners, or to form a cavity for the implantation of an implant or fastener. The stent comprises, in one preferred embodiment, a plurality of elongate generally cylindrical drill guide bodies secured each other by a pair of positioning bars. Each drill guide body is a generally cylindrical body having a length and at least one diameter. If the body is a true cylinder, it has one diameter. If it is only generally cylindrical, it may have a major diameter and a minor diameter. While the body may be any shape, it is convenient if the body is so configured and constructed as to define an imaginary cylinder axis through the length there through. Typically, the body would be a right cylinder; however, precise geometry is not important; indeed, as mentioned, the body does not have to be cylindrical at all. Preferably, however, the body is constructed to define a pilot guide bore for guiding a drill substantially along said axis for guiding a drill when the rigid guide is completed. The body also defines a pair of lateral bores substantially perpendicular to said pilot guide bore, each lateral bore lying substantially along chord of said drill guide body disposed on opposite sides of the pilot guide bore. The drill guide bodies are connected together by a bar or pair of guide bars constructed and configured to fit snugly in the lateral bores in the drill guide bodies extending through the lateral bores of said drill guide bodies that secure the drill guide bodies together to permit the drill guide bodies to be positioned and spaced relative to each other and to permit the drill guide bodies to be axially oriented relative to each other. The assembly of drill guide bodies and bars may be pre-assembled and adjusted as needed to conform to the curvature of the bone into which fasteners are to be installed. The bars may be rigid but capable of being bent using conventional tools, they may be configured in a curve and various lengths and curvatures may be provided, or they may be relatively soft and bendable by hand or using forceps, etc., at the time of installation. The stent can be prefabricated and sold as an adjustable stent, or may be custom created to fit any curvature, configuration, etc., during or after surgery. Thus, the drill guide bodies can be position linearly, in a zigzag pattern or in any other pattern. Similarly, the drill guide bodies can be spaced regularly or irregularly. The axes of the drill guide bodies can be parallel or oriented at any desired angle respect to each other, i.e., axially oriented as desired.

The invention is also embodied in a completed rigid drill guide formed by placing a stent as described on the surface for which a reciprocal replication is desired, positioning, spacing and orienting the individual drill guide bodies by bending the positioning bars and moving the drill guide bodies along the positioning bars so that each drill guide body is positioned, spaced and oriented with respect to any other drill guide body and the bone into which the holes are to be drilled so that when a drill is passed through the pilot guide bore in the drill guide body the drill will drill a hole in the proper position and spacing and correct orientation.

The method just described for forming a rigid guide is also an embodiment of the invention, as is the preparation of the stent.

These and other characteristics of the invention will become more clear from the exemplary drawings and the description of the exemplary embodiment which follow.

DESCRIPTION OF THE PREFERRED EMBODIMENTS

Figure 1:
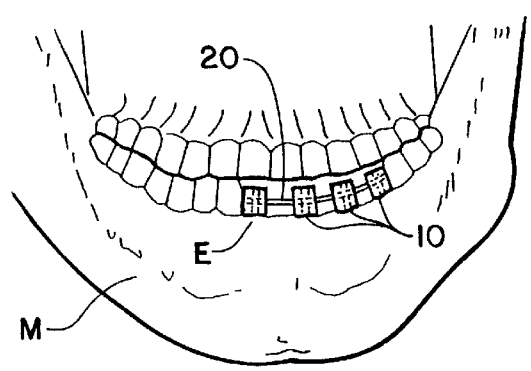
FIG. 1 depicts, as an example only, the first step in the fabrication of a drill guide specifically for use at a specific site on or overlaying a patient's bone structure for guiding the drilling of guide holes into the bone at the desired spacing, location and orientation.

The invention is described in reference to drawings that depict exemplary embodiments of the invention. The drawings and the description do not, however, circumscribe the invention; rather, they describe a presently preferred embodiment. With time and experience the invention and its embodiments will, no doubt, be refined as to materials and structural details; accordingly, the invention is not limited by the examples given or depicted in the drawings.

The present invention may be used to install virtually any type or system of implants, prostheses and surgical appliances. In the following discussion, reference will be made an "implant" which may be a screw-type implant, a cylindrical implant, a blade type implant, or any of the myriad of variants upon known implants. The drawings and description are merely exemplary and are not in anyway limiting as to the invention.

Referring first to FIG. 1, the invention is shown being used in a first step to provide a drill guide into an edentulous portion E of the mandible M of a patient. A plurality of drill guide bodies 10 are connected together on a pair of wires or rods, one of which is shown at 20. The wire or rods, referred to simply as positioning rods hereinafter, are sufficiently bendable or are adapted to conform to the curvature of the bone into which the guide holes are to be drilled.

The combination of positioning rods connecting a plurality of drill guide bodies forms a stent for the ultimate drill guide. The drill guide bodies are spaced along the positioning rod and positioned relative to each other by bending the positioning rods or using positioning rods that are adapted to conform to the curvature of the bone. The axial orientation of the drill guide bodies can also be adjusted by bending the positioning rods.

Figure 2:
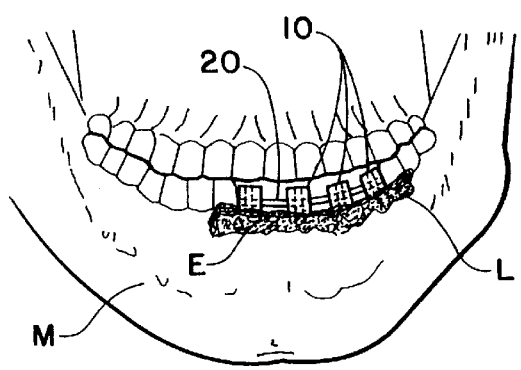
FIG. 2 depicts the drill guide of FIG. 1.

With the stent in place, as shown in FIG. 1, a moldable luting material L is applied to the stent to encase a portion of the guide cylinder, as shown in FIG. 2. The luting material may encase all but the distal end of the drill guide bodies, although the proximal end, which would normally reside against or adjacent the patients tissue or bone, is usually left free of luting material. Once the luting material hardens, the drill guide for drilling guide holes, wire holes, screw or fastener holes, is ready for use.

Figure 3A:
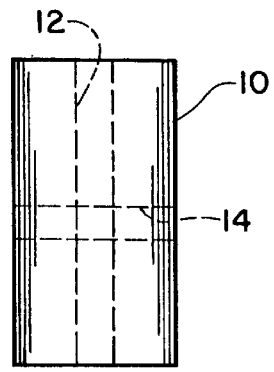
FIGS. 3A, 3B and 3C depict in side elevation, top plan and rotated side elevational view a drill guide body according to this invention.
Figure 3B:
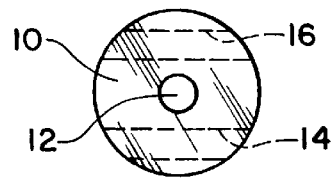
Figure 3C:
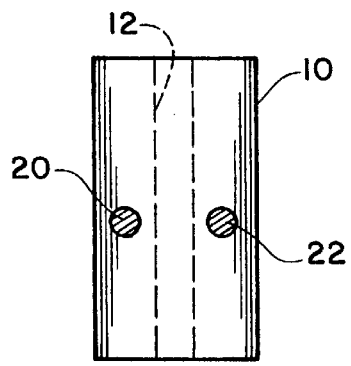

Each of the drill guides comprises a body 10, as best shown in FIGS. 3A, 3B and 3C, that is configured to define a generally central pilot guide bore 12 extending through the body. The body also defines a pair of lateral bores 14 and 16, one on each side of the pilot guide bore 12, which extend generally perpendicular to the axis of the cylinder and parallel to each other. As shown in FIG. 3C, the guide bars 20 and 22 fit snugly through the lateral bores 14 and 16.

Figure 4:
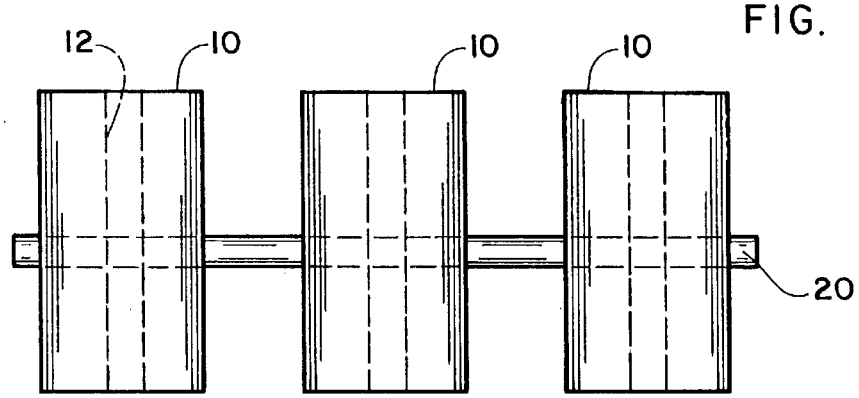
FIG. 4 depicts a plurality of drill guide bodies attached together by wires or bars to form the guiding member of the drill guide shown in FIG. 2.

As shown in FIG. 4, the stent comprises a plurality of drill guide bodies 10 connected together by a pair of positioning bars 20 and 22, the drill guide bodies and positioning bars being so constructed and configured as to permit the drill guide bodies to be spaced at variable desired distances from each other, to be positioned relative to each other by using bars of any predetermined shape and length so the stent when formed conforms to the bone curvature or by bending the positioning bars and the drill guide bodies are properly oriented relative to the bone, or bending the positioning bars to axially orient and position the drill guide bodies relative to each other. The ends of the bars may be formed with a compression crimp end to fit firmly and essentially non-removably in the drill guide bodies.

The positioning bars may be freely bendable dead soft material with little or no resilience or memory so as to permit easy positioning and orienting of the drill guide bodies along complex curves, or the like. On the other hand, where greater strength or rigidity is required, the positioning bars may be formed of slightly or significantly resilient material. Resilient positioning bars may, for example, be useful where the desired configuration is arcuate and where the bars may be anchored, e.g., to an adjacent tooth as shown in FIGS. 1 and 2, while the luting material is applied and hardened or while the stent is fixed with any other means. The stent may, for example, be secured by screws, clamps, wires or other fixtures to adjacent boney structure, teeth, etc., in lieu of or in addition to the use of luting material. The luting material is simply a convenient example of a means for rigidifying and/or securing the stent.

The drill guide bodies may be made of any hard material, e.g., stainless steel, titanium, acrylic resins, polycarbonates, nylons, etc. The drill guide bodies may be reusable or disposable. Thus, materials are not a critical aspect of the invention and those skilled in the art may select materials to meet environmental requirements, e.g., capable of being sterilized, etc. Likewise, the guide bars may be made of stainless steel, silver alloys, etc. that meet environmental requirements and which are as soft or resilient as required by the particular application.

Luting materials and techniques are, of course, well known. Examples of commercially available luting materials include Vitremer™ Luting Cement, sold by 3M Dental Products Division, St. Paul, Minn.; Advance Hybrid Ionomer Cement, sold by L.D. Calk Division, Dentsply International, Milford, Del.; and Fuji Duet Reinforced Multipurpose Glass Ionomer Cement, sold by GC America, Chicago, Ill. A comparative report on such materials has been published by Dr. Mark Latta of Creighton University. Light cured composite materials are becoming popular and are commercial available from dental supply houses.

Once the stent is formed by spacing, positioning and orienting the drill guide bodies, as described, and the luting material has been applied and hardened, a rigid guide for drilling holes at the precise location and orientation required for the installation of a surgical appliance, prosthesis, stent for supporting prostheses, etc., is available. In the example described, the rigid drill guide is positioned at the site to be drilled and a conventional dental or surgical drill is passed through the pilot guide passage 12 and into the bone.

It will be observed in FIG. 2 that the rigidifying means, e.g., luting compound, may, if desired, extend beyond the end or ends of the stent per se and onto the adjacent teeth. While this extension is not necessary in most instance, the drawing illustrates the use of the stent or guide cylinder using an adjacent structure for basic or additional support or strength. For example, a single guide cylinder may be used between adjacent teeth or other structures to provide a drill guide.

Figure 5:
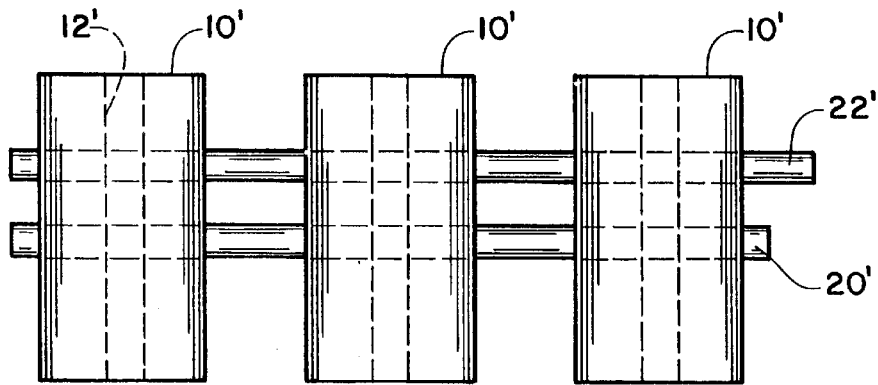
FIG. 5 depicts an alternative embodiment of the stent of this invention.
Figure 6:
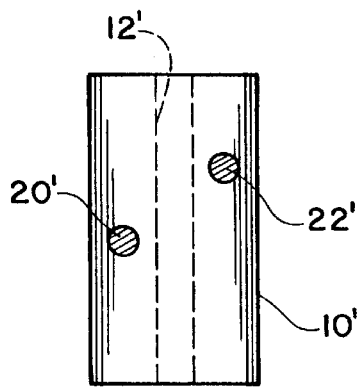
FIG. 6 depicts a screw guide of the type used in the alternative embodiment shown in FIG. 5.

FIGS. 5 and 6 depict an alternative version of the invention in which the passages for the bars are at different positions, as compared with the preceding example. One or more bars may be used and they bars may be attached to the drill guide bodies symmetrically as in the first example or asymmetrically as in the second example, or in any desired arrangement.

The stent may be rigidified during construction by incorporating the rigidifying means into the bars. For example, if pre-shaped rigid bars that define structure for rigid attachment to the drill guide bodies are used, the stent is a rigid drill guide when completed. The bars may be round or square, or any other shape, in cross-section and if so sized as to press-fit to the drill guide body or bodies forms a rigid drill guide when complete. Thus, any rigidifying means may be used.

Fundamental to the invention is the stent for forming a rigid guide that has a surface that is a reciprocal replication of the surface of a portion of a patient's boney structure into which one or more holes are to be drilled at predetermined locations. The ultimate rigid mold, which typically is for guiding the drilling of plural holes in boney structure, has a surface which will fit snugly against the surface of the patient's body into which holes are to be drilled. Thus an impression mold taken of the surface of interest would reciprocally replicate the surface. The surface may be a tissue surface, e.g. tissue covering an edentulous portion of the patient's jaw, or skin or tissue covering a simple bone fracture or a compound fracture, anatomical prosthesis, etc.

Figure 7:
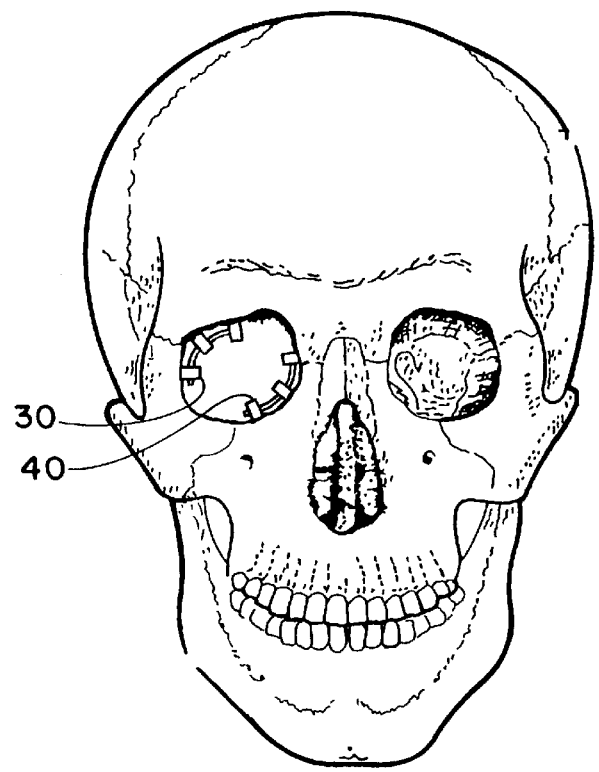
FIG. 7 depicts, in simplified form for better illustration, the application of the stent of this invention to the boney structure surrounding the eye for attaching, for example with magnets, a prosthetic eye, simply to illustrate another of the many applications in which the invention may be used.

FIG. 7 depicts the use of a pair of stents 30 and 40 of this invention for providing guides for drilling into the boney structure surrounding the eye to provide means for positioning a prosthetic eye. Prostheses or stents may be formed and used for virtually any procedure that involves drilling into boney tissue or in forming any prosthetic device, whether external or internal.

The surface may, in some surgical procedures, be the surface of the bone into which the holes are to be drilled, or any other surface that is adjacent or overlays a boney structure into which holes are to be drilled. In surgical procedures, it is frequently necessary that holes be drilled in precise, predetermined position, spacing and orientation to match screw holes or wire holes or to permit the placement of securing means, such screws, implants, pins, etc. It is often necessary to form a cavity for the implantation of an appliance, e.g., a dental implant, a bone implant, etc. The stent comprises a plurality drill guide bodies secured each other by a pair of positioning bars. The body is, in the most preferred but not required form, so configured and constructed as to define an imaginary cylinder axis through the length there through. The length may be more than, equal to, or less than the diameter of the body . Typically, the body would be a right cylinder; however precise geometry is not important. The body is constructed to define a pilot guide bore for guiding a drill substantially along said axis for guiding a drill when the rigid guide is completed. The size of the pilot guide bore will depend on the size of drill to be used and may vary; however, as a set of components, it is often satisfactory to provide a drill of a given size and drill guide bodies having a pilot guide bore of substantially the same size, e.g. 2 mm, into which the drill will fit snugly. The body also defines a pair of lateral bores substantially perpendicular to said pilot guide bore, each lateral bore lying substantially along chord of said drill guide body disposed on opposite sides of the pilot guide bore. The drill guide bodies are connected together by one or more guide bars constructed and configured to fit snugly, and moveably if desired, in the lateral bores in the drill guide bodies extending through the lateral bores of said drill guide bodies that secure the drill guide bodies together to permit the drill guide bodies to be positioned and spaced relative to each other and to permit the drill guide bodies to be axially oriented relative to each other. Thus, the drill guide bodies can be position linearly, in a zig-zag pattern or in any other pattern. Similarly, the drill guide bodies can be spaced regularly or irregularly. The axes of the drill guide bodies can be parallel or oriented at any desired angle respect to each other, i.e. axially oriented as desired.

Referring now to FIGS. 8, 9A, 9B and 10, it will be apparent that virtually any mechanical securing device concept may be applied in securing the drill guide bodies to the positioning rods.

Figure 8:
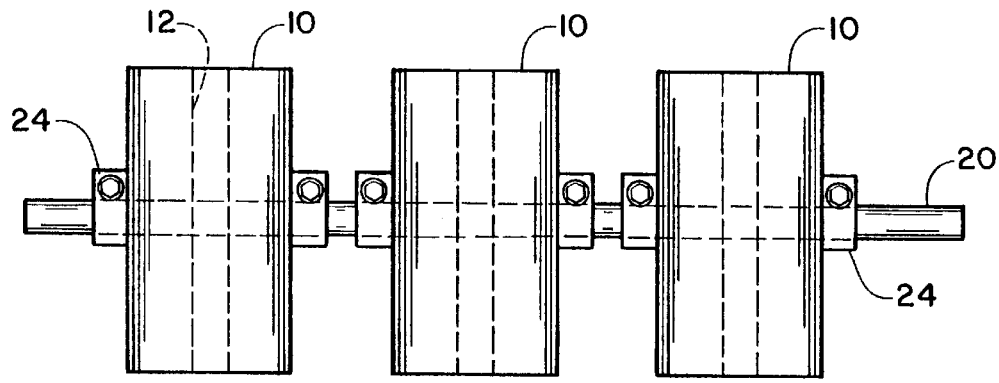
FIG. 8 depicts a drill guide wherein the drill guide bodies are secured to the positioning rods by a mechanical clamp.
Figure 9A:
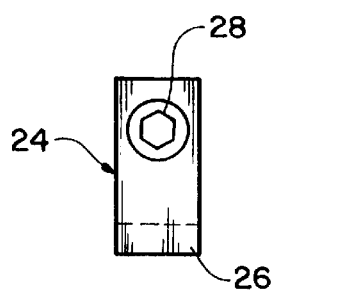
FIGS. 9A and 9B show, respectively, a greatly enlarged end view and side view of the mechanical clamp depicted in use in FIG. 8.
Figure 9B:
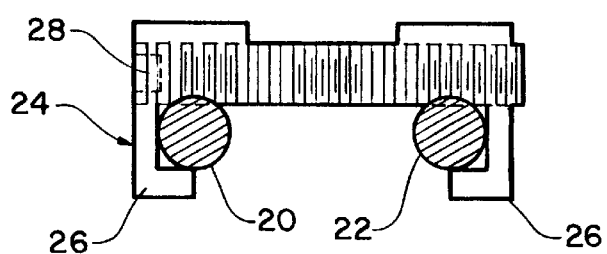

In FIGS. 8, 9A and 9B, a screw operated clamp comprises the securing means 24. As best shown in FIGS. 9A and 9B, the securing means comprises a pair of clamp members threadably received on a screw 28 which, in this example, has a hex opening in one or both ends for operating the screw. As shown in FIG. 9B when the clamps extend over and encompass the guide bars and the operating screw 28 is turned in one direction the clamps engage the positioning rods and force the screw against the positioning rods. The screw is of a material as hard as or harder than that of the positioning rods and forms threads in the positioning material as the clamps close upon the positioning rods. This is, of course, but one example of an innumerable number of clamps that can be sized and configured to be used as securing means.

Figure 10:
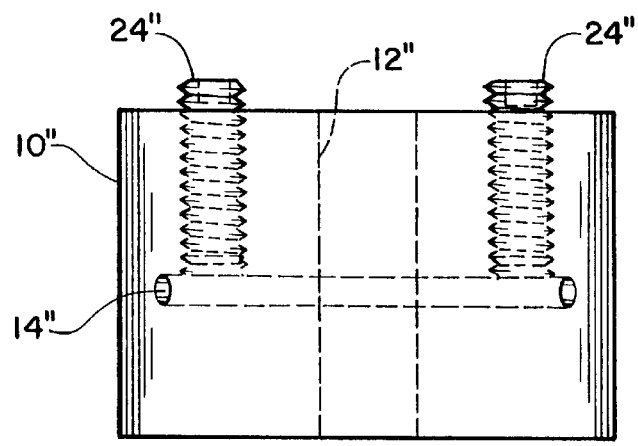
FIG. 10 shows a cylindrical drill guide body in which the axis is shorter than the diameter and wherein the securing means is a set screw threadably received in the drill guide body for engaging the positioning rod.

In FIG. 10, simply to illustrate the concept of short drill guide bodies, the drill guide body 10" has a longitudinal axis shorter than the diameter of the generally cylindrical drill guide body. The pilot guide bore 12" extends generally coaxially of the drill guide body in this embodiment, though the pilot guide bore may be offset from the center. The lateral bore 14" extends generally perpendicularly to and is displaced from the pilot guide bore and receives the positioning rod. In this example, the lateral bores are at the same plane and parallel with each other, although the same result can be obtained using offset lateral bores of the type shown in FIG. 6. A pair of set screws 24" are threadably received in a passage formed in the body to intersect the respective lateral bores. The set screws 24" typically have a hex opening and are generally of the type referred to as Allen screws. When tightened, the ends of the set screws rigidly secure the positioning rod in the lateral bores and firmly fixes the position of the drill guide body on the positioning rod.

The foregoing are, of course, exemplary only and the nature of the mechanical securing means is not critical to the invention.

The method of carrying out the invention to prepare a stent for a rigid guide will be understood from the foregoing description. The surgeon simply fits one or more drill guide bodies, usually from two to ten such guides being used, onto the positioning bars and places the assembly adjacent the surface onto which the rigid guide is to fit. The position, spacing and orientation of the holes will have been determined or are determined visually or by X-ray for example. By the time the stent is formed, the position, spacing and orientation of the holes has been predetermined and the drill guide bodies are moved along the positioning bars to obtain proper spacing and the positioning bars are bent to obtain proper positioning and orientation so that the pilot guide bores in the drill guide bodies will direct a drill to the correct location at the proper angle. The stent could be used as formed, of course, but it is desirable and usually necessary to form a rigid guide at least one surface of which will mate with the surface into which or covering the bones into which the holes are to be drilled in order to maintain proper position during drilling.

The stent may be used to guide holes for affixing a prosthesis to the bone or may comprise the prosthesis per se. Referring momentarily to FIG. 7, for example, it will be apparent that the stents 30 and 40 would securely and rigidly fix the position of bone fragments if the adjacent bone had been fractured. Thus, the stent is the prosthesis. A further advantage is obtainable using the stent as a prosthetic device. Osteotaxis can be performed by securing the individual bodies to individual bone structures and then forming the stent so as to properly position the bone fragments to allow the bones to grow together again.

In one embodiment, the forming of the rigid guide or stent adds to the foregoing method the step of securing the drill guide bodies to the positioning bars with a mechanical securing means, such as the exemplary securing means shown and described, to position the drill guide bodies adjacent the surface to which the guide is to be mated. As pointed out, the securing clamps and set screw arrangements shown are merely exemplary and any means that secures the drill guide bodies in a fixed and firm relationship to the positioning bar or bars may be used.

In another embodiment, for forming the rigid guide, usually for guiding the drilling of plural holes, adds to the foregoing method the step of encasing at least the portions of the drill guide bodies adjacent the surface to which the guide is to be mated in luting material and hardening luting material, e.g., with ultraviolet light, or permitting the luting material to set. Substantially all of the drill guide bodies and positioning bars may be encased in luting materials so long as access to the pilot guide bores can be gained for guiding the drill during use.

In one form, of course, the invention is also embodied in a completed rigid drill guide formed by placing a stent as described on the surface for which a reciprocal replication is desired, positioning, spacing and orienting the individual drill guide bodies by bending the positioning bars and moving the drill guide bodies along the positioning bars so that each drill guide body is positioned, spaced and oriented with respect to any other drill guide body and the bone into which the holes are to be drilled so that when a drill is passed through the pilot guide bore in the drill guide body the drill will drill a hole in the proper position and spacing and correct orientation followed by making the stent rigid with luting material as described.

The invention is of general application and may be used in most surgical procedures in which holes are drilled at predetermined positions and spacing and orientation relative to each other and/or to the bone into which the holes are drilled.

INDUSTRIAL APPLICATION

This invention finds utility and applicability in the surgical appliance field.

What is claimed is:

1. A stent for forming a guide shaped as the reciprocal replication of the surface of a portion of a patient's boney structure into which holes are to be drilled at predetermined locations, spacing and orientation, comprising, in combination:

a plurality of drill guide bodies, each such drill guide body being a generally cylindrical elongate body having first and second ends, a length and a diameter, the length being at least about twice as great as the diameter, said body being so configured and constructed as to define an imaginary axis generally centrally through the length thereof and being configured and constructed to define a pilot guide bore substantially along said axis for guiding a drill during use and also being configured and constructed to define through the elongate generally cylindrical body between said first and second ends at least one lateral bore oriented substantially perpendicular to said pilot guide bore and passing through the body substantially along chord of said body disposed on one side of the pilot guide bore; and a guide bar constructed and configured to fit snugly in the lateral bores in the drill guide bodies extending through the lateral bore of said drill guide bodies for securing said drill guide bodies together to permit the drill guide bodies to be position and spaced relative to each other and to permit the drill guide bodies to be axially oriented relative to each other.

2. A stent for forming a guide shaped as the reciprocal replication of the surface of a portion of a patient's boney structure into which holes are to be drilled at predetermined locations, spacing and orientation, comprising, in combination:

a plurality of drill guide bodies, each such drill guide body being a body having a length so configured and constructed as to define an imaginary axis through the length thereof and forming a pilot guide bore for guiding a drill substantially along said axis and at least two lateral bore substantially perpendicular to said pilot guide bore substantially along chord of said drill guide body disposed on opposite sides of the pilot guide bore; and a pair of guide bars constructed and configured to fit snugly in the lateral bores in the drill guide bodies extending through the lateral bores of said drill guide bodies for securing said drill guide bodies together to permit the drill guide bodies to be position and spaced relative to each other and to permit the drill guide bodies to be axially oriented relative to each other.

3. A stent for forming a guide shaped as the reciprocal replication of the surface of a portion of a patient's boney structure into which holes are to be drilled at predetermined locations, spacing and orientation, comprising, in combination:

a plurality of drill guide bodies, each such drill guide body being a body having a length so configured and constructed as to define an imaginary axis through the length thereof and forming a pilot guide bore for guiding a drill substantially along said axis and at least two lateral bore substantially perpendicular to said pilot guide bore substantially along chord of said drill guide body disposed on opposite sides of the pilot guide bore;

a pair of guide bars constructed and configured to fit snugly in the lateral bores in the drill guide bodies extending through the lateral bores of said drill guide bodies for securing said drill guide bodies together to permit the drill guide bodies to be position and spaced relative to each other and to permit the drill guide bodies to be axially oriented relative to each other; and rigidifying means for making the stent rigid for fixedly positioning, spacing and orienting the drill guide bodies to guide a drill through the respective drill guide bodies at a predetermined orientation to a predetermined location in a patient's boney structure.

4. A stent for forming a guide shaped as the reciprocal replication of the surface of a portion of a patient's boney structure into which holes are to be drilled at predetermined locations, spacing and orientation, comprising, in combination:

a plurality of drill guide bodies, each such drill guide body being a generally cylindrical elongate body having first and second ends, a length and a diameter, the length being at least about twice as great as the diameter, said body being so configured and constructed as to define an imaginary axis generally centrally through the length thereof and being configured and constructed to define a pilot guide bore substantially along said axis for guiding a drill during use and also being configured and constructed to define through the elongate generally cylindrical body between said first and second ends at least one lateral bore oriented substantially perpendicular to said pilot guide bore and passing through the body substantially along chord of said body disposed on one side of the pilot guide bore;

a guide bar constructed and configured to fit snugly in the lateral bores in the drill guide bodies extending through the lateral bore of said drill guide bodies for securing said drill guide bodies together to permit the drill guide bodies to be position and spaced relative to each other and to permit the drill guide bodies to be axially oriented relative to each other; and rigidifying means for making the stent rigid for fixedly positioning, spacing and orienting the drill guide bodies to guide a drill through the respective drill guide bodies at a predetermined orientation to a predetermined location in a patient's boney structure.

5. A method for forming a stent for a rigid guide having a surface that is a reciprocal replication of the surface of a portion of a patient's boney structure into which holes are to be drilled at predetermined locations, spacing and orientation, comprising:

fitting a plurality of drill guide bodies onto at least one positioning bar, each such drill guide body being a generally cylindrical elongate body having first and second ends, a length and a diameter, the length being at least about twice as great as the diameter, said body being so configured and constructed as to define an imaginary axis generally centrally through the length thereof and being configured and constructed to define a pilot guide bore substantially along said axis for guiding a drill during use and also being configured and constructed to define through the elongate generally cylindrical body between said first and second ends at least one lateral bore oriented substantially perpendicular to said pilot guide bore and passing through the body substantially along chord of said body disposed on one side of the pilot guide bore, the positioning bar being configured to fit snugly in the lateral bores in the drill guide bodies extending through the lateral bores of said drill guide bodies for securing said drill guide bodies together to permit the drill guide bodies to be position and spaced relative to each other and to permit the drill guide bodies to be axially oriented relative to each other; and moving the drill guide bodies on the positioning bars to position, space and orient the drill guide bodies for guiding drills through the pilot guide bores there through to the desired position in a boney structure of a patient and at the angle at a hole in the patient's boney structure is to be drilled.

6. A method for forming a rigid guide having a surface that is a reciprocal replication of the surface of a portion of a patient's boney structure into which holes are to be drilled at predetermined locations, spacing and orientation, comprising:

fitting a plurality of drill guide bodies onto a pair of positioning bars, each such drill guide body being a body having a length so configured and constructed as to define an imaginary axis through the length thereof and forming a pilot guide bore for guiding a drill substantially along said axis and at least two lateral bore substantially perpendicular to said pilot guide bore substantially along chord of said drill guide body disposed on opposite sides of the pilot guide bore, each of the positioning bars being a bendable guide bar constructed and configured to fit snugly in the lateral bores in the drill guide bodies extending through the lateral bores of said drill guide bodies for securing said drill guide bodies together to permit the drill guide bodies to be position and spaced relative to each other and to permit the drill guide bodies to be axially oriented relative to each other;

moving the drill guide bodies on the positioning bars to position, space and orient the drill guide bodies for guiding drills through the pilot guide bores there through to the desired position in a boney structure of a patient and at the angle at a hole in the patient's boney structure is to be drilled; and rigidifying the stent for fixedly positioning, spacing and orienting the drill guide bodies to guide a drill through the respective drill guide bodies at a predetermined orientation to a predetermined location in a patient's boney structure.

7. A stent for forming a guide shaped as the reciprocal replication of the surface of a portion of a patient's boney structure into which holes are to be drilled at predetermined locations, spacing and orientation, comprising, in combination:

a plurality of drill guide bodies, each such drill guide body being an elongate body having first and second ends, a length and a diameter, the length being at least about twice as great as the diameter, said body being so configured and constructed as to define an imaginary axis generally centrally through the length thereof and being configured and constructed to define a pilot guide bore substantially along said axis for guiding a drill during use and also being configured and constructed to define through the elongate body between said first and second ends at least one lateral bore oriented substantially perpendicular to said pilot guide bore and passing through the body substantially along chord of said body disposed on one side of the pilot guide bore; and a guide bar constructed and configured to fit snugly in the lateral bores in the drill guide bodies extending through the lateral bore of said drill guide bodies for securing said drill guide bodies together to permit the drill guide bodies to be position and spaced relative to each other and to permit the drill guide bodies to be axially oriented relative to each other.

8. A prosthesis shaped as the reciprocal replication of the surface of a portion of a patient's boney structure into which holes are to be drilled at predetermined locations, spacing and orientation, comprising, in combination:

a plurality of drill guide bodies, each such drill guide body being a body having a length so configured and constructed as to define an imaginary axis through the length thereof and forming a pilot guide bore for guiding a drill substantially along said axis and at least two lateral bore substantially perpendicular to said pilot guide bore substantially along chord of said drill guide body disposed on opposite sides of the pilot guide bore; and at least one guide bar constructed and configured to fit snugly in the lateral bores in the drill guide bodies extending through the lateral bore of said drill guide bodies for securing said drill guide bodies together to permit the drill guide bodies to be position and spaced relative to each other and to permit the drill guide bodies to be axially oriented relative to each other.

* * * * *